United States Patent [19]

Hatada et al.

[11] 4,337,768

[45] Jul. 6, 1982

[54] POLYVINYL CHLORIDE SHEET AND METHOD OF MAKING THE SAME

[75] Inventors: Kenji Hatada; Hiroaki Kobayashi, both of Otsu, Japan

[73] Assignee: Toray Industries, Inc., Tokyo, Japan

[21] Appl. No.: 166,581

[22] Filed: Jul. 7, 1980

[30] Foreign Application Priority Data

Feb. 26, 1980 [JP] Japan ................................. 55/22270

[51] Int. Cl.³ ............................................ A61M 5/14
[52] U.S. Cl. ............................. 128/214 D; 428/339; 428/409; 428/421; 428/35; 204/165; 204/199
[58] Field of Search ................ 428/35, 520, 522, 336, 428/339, 421, 220, 212, 409; 128/214 D; 204/165, 199

[56] References Cited

U.S. PATENT DOCUMENTS 3,429,732  2/1969  Baitinger ............................ 428/520

Primary Examiner—George F. Lesmes
Assistant Examiner—B. K. Johnson
Attorney, Agent, or Firm—Austin R. Miller

[57] ABSTRACT

This invention relates to a polyvinyl chloride sheet comprising crosslinked thin layer(s) and uncrosslinked layer(s), at least one surface of the sheet being a crosslinked layer. The thickness of the said crosslinked layer ranges between about 0.05 to about 2 microns, and the degree of the chlorination of the said layer is not greater than about 45% of that of the uncrosslinked layer, and the degree of heat shrinkage is not greater than about 1%. This sheet provides many advantages for blood bags and infusion bags.

9 Claims, 4 Drawing Figures

POLYVINYL CHLORIDE SHEET AND METHOD OF MAKING THE SAME

BACKGROUND OF THE INVENTION

This invention relates to a polyvinyl chloride sheet and to blood bags, and infusion bags made therefrom, the surfaces of which are modified so that the diffusion of plasticizer to the surface is suppressed and compatibility of the polyvinyl chloride with respect to the contents of the bags is improved.

It is well known that crosslinked thin layers on the surfaces of chlorine-containing vinyl polymers such as polyvinyl chloride and polyvinylidene chloride, formed by glow discharge or UV radiation, act as barriers to migration of lower molecular weight substances such as monomers, plasticizers and additives to the surface. This surface modification method is considered to be very useful, because hardening of said resins and environmental contamination caused by diffusion and release of the plasticizer are serious defects.

However we have found during our study of this type of surface modification that the modified surface becomes rough and loses transparency to polarized light when the polyvinyl chloride sheet with a thin crosslinked layer is heated above its softening point. The transparency of the sheet is a very important property for many applications. For example, if medical bags such as blood bags and infusion bags lose transparency during the heating process involved in autoclave sterilization or during the process of ethylene oxide gas sterilization, the contents of the bag cannot substantially be observed through the bag. An important object of this invention is to provide a transparent polyvinyl chloride sheet having a high quality crosslinked thin layer on its surface.

At present, many blood bags are made of polyvinyl chloride sheet because of its flexibility and other well-balanced properties. However, the compatibility problem and the decrease of numbers and activities of platelets that is encountered during the preservation still remain unsolved. This invention provides blood bags having improved use as preservatives of platelets through the use of specific gases during glow discharge, and through the use of specific anticoagulation agents. Therefore, the creation of polyvinyl chloride sheets and blood bags made therefrom, having improved biocompatibility, is another important object of this invention.

Usually a plastic surface treated by glow discharge becomes hydrophilic (good wettability), which can be a valuable or a detrimental property, depending on the intended application. For the use of blood bags and infusion bags, a reduced diffusion rate of water is preferable. The glow discharge treatments heretofore carried out have not resulted in low diffusion rates. Furthermore, we have encountered a serious problem in that emulsified lipids contained in a high calorie infusion increase in size due to interaction between the emulsion and the hydrophilic surface treated by ordinary glow discharge. A further object of this invention is to provide a modified polyvinyl chloride sheet which retards the diffusion of the plasticizer and whose surface is hydrophobic.

Other objects of this invention will appear in further detail hereinafter and in the following description.

DETAILED DESCRIPTION OF THE INVENTION

The polyvinyl chloride sheet in the present invention is composed of a crosslinked thin layer on at least one surface and an uncrosslinked layer covered by the crosslinked thin layer. The said crosslinked thin layer may range from about 0.05 to 2 microns in thickness and the degree of chlorination should not be greater than about 45% of that of the uncrosslinked layer. This sheet also has a heat shrinkage value of not greater than about 1%. The resin of the sheet of this invention consists mainly of polyvinyl chloride, with additives such as plasticizers and/or anti-oxidants, etc., depending on the specific application.

Films are also included within the definition of the term "sheets" as used in the practice of this invention.

The crosslinked thin layer of this invention is about 0.05 micron to about 2 microns thick and not greater than about 45% of the degree of chlorination of that of the uncrosslinked layer, preferably about 0.1 to 1 micron thick and not greater than about 30% of the original chlorination degree.

The reasons underlying the fact the above specified crosslinked thin layer more effectively prevents low molecular substances from diffusing to the surface is not completely understood. However, our diligent studies have suggested that the crosslinking of the polyvinyl chloride sheet surface takes place as the result of a dechlorination reaction; a degree of chlorination of more than about 45% of the original means that the crosslinking is so premature that lower molecular weight substances can still diffuse in the layer at a reasonable rate. In fact, the thin crosslinked layer (gel layer) can be swollen in tetrahydrofuran at a higher degree of chlorination, according to our observations.

The degree of chlorination can be measured quantitatively by such methods as molecular analysis of chlorine atoms, XPS (X-ray photo electron spectroscopy) analysis and XMA (X-ray micro analysis). Molecular analysis is carried out by burning the samples completely in an oxygen flask forming chlorine gas, which is absorbed in a hydrazine solution and titrated by a potentiometer using silver nitrate. In XPS analysis, the degree of chlorination is measured by the peak area ratio of $C_{1s}$ and $Cl_{2p}$. $(Cl_{2p}/C_{1s})$. In XMA analysis, the chlorine concentration can be measured directly. These three methods have been tried respectively for crosslinked thin layer samples and uncrosslinked (original) polyvinyl chloride samples, and the conclusion is that the similar value of degree of chlorination (the ratio of crosslinked layer to the original) can be measured by these three methods. The crosslinked part and the uncrosslinked part can be easily separated using tetrahydrofuran.

Crosslinked layer thickness of less than 0.05 micron is believed to be an insufficient barrier to low molecular weight substances. On the other hand, if the thickness is more than 2 microns, the crosslinked layer gels harden and a small mechanical deformation of a treated sheet causes formation of micro cracks, through which small molecular weight substances diffuse freely. When a polyvinyl chloride sheet having a crosslinked layer more than 2 microns thick is dissolved in tetrahydrofuran, yellowish needle-like undissolved substances separating from the bulk layer can be observed promptly after the immersion of the sample.

The thickness of the crosslinked layer can be measured by an electron microscope. A sample is prepared by dyeing the sheet with $O_sO_4$ and slicing it after usual packing procedures. The crosslinked layer consists of two layers: an undyed layer on the top surface and a dyed layer. The thickness of the crosslinked layer is defined as the sum of the thicknesses of the above two layers. The thickness can be more easily determined by weighing the gel mass of a specific area assuming its specific gravity is 1.2. This method is, however, not always accurate because of the specific gravity strongly depends on the amount of additives and the degree of crosslinking. Based on our experimental results this "gel weight" method has an error of about 20%, compared with the electron microscope method, though it is a very convenient and easy method.

The polyvinyl chloride sheet is not necessarily covered by the crosslinked layer in this invention. The sheet can be treated partly or locally depending on need.

The heat shrinkage of the sheet in this invention must be less than about 1%. If the heat shrinkage is more than about 1%, the crosslinked surface layer shows a striped pattern caused by uneven deformation after specific thermal history. This phenomenon, accompanied by loss of transparency, is probably due to differing thermal shrinkage (irreversible thermal dimensional change) between the crosslinked layer and the uncrosslinked layer. In sheets with a heat shrinkage of not greater than about 1%, the striped pattern is not so obvious and the transparency remains as it was before the treatment. In sheets with less than 0.5% heat shrinkage, no change can be observed, even using microscopy. So, in order to keep the treated sheet transparent, the sheet must have a heat shrinkage of less than about 1%, preferably less than about 0.5%.

Heat shrinkage in accordance with this invention is measured as follows: Three sheet samples are taken from the treated polyvinyl chloride sheet and marked, as shown in FIG. 1, so that the distances AF, BG, CH and AC, DE, FH are all 100 mm. These samples are heated in an air circulating oven at 100°±2° C. for 10 minutes, and are taken out and cooled down to room temperature. The lengths of AF, BG, CH and AC, DE, FH are measured. Taking an average of AF, BG and CH, the longitudinal distance between marks is computed and set equal to l (mm), and longitudinal heat shrinkage, S (%), is calculated as follows:

$$S = ((100 - l)/100) \times 100$$

Similarly, by taking an average of AC, DE, FH, computation of the transverse distance l (mm) leads to transverse heat shrinkage S (%).

The barrier effect of glow discharge treatment is measured as follows: Placing an extraction apparatus on the polyvinyl chloride sheet with a "Teflon" sheet ring in between, said apparatus, filled with 13.6 g (20 cc) n-hexane having 11.34 $cm^2$ extraction area, is kept at 40° C. for 2 hours. DOP (dioctyl phthalate or di-2-ethyl hexyl phthalate), the most popular plasticizer for polyvinyl chloride, extracted in n-hexane, is measured quantitatively by gas chromatography.

We have discovered that the crosslinked layer is partly fluorinated when the fluorine gas is mixed in the glow discharge gas. A fluorinated crosslinked surface has a hydrophobic property reducing the penetration coefficient of moisture as well as reducing the diffusion coefficient of plasticizer. To achieve this effect, it is preferable that the number of fluorine atoms to carbon atoms be not less than 10% on the surface. Of course, the polyvinyl chloride sheet is not necessarily covered by the crosslinked layer completely. For example, the blood bag may be designed so that its inside surface is modified for improving biocompatibility and its outside surface is modified to prevent moisture penetration, both by fluorination.

This invention provides heat treatment of the polyvinyl chloride sheet to reduce its heat shrinkage to a value not greater than about 1%, and exposing it to a glow discharge at a pressure of about $10^{-2}$ to 10 torrs and at an electric supply frequency of about 1 to 1,000 kHz. Heat treatment is usually carried out by hot rolling.

One example of glow discharge treatment is illustrated as shown in FIG. 2. In this FIGS. 1, 2 and 3 are a web transportation roll (grounded), a web feeding roll, and a winding roll, respectively. The members 6, 9 and 10 are a glass coated discharge electrode (rod-like), a matching network, and a high voltage power generator, respectively, 8 is a glow discharge equipment case containing items 1, 2, 3, and 6. 4 is the glow discharge gas inlet, and 5 is the outlet. 7 is a sheet being treated.

The sheet is loaded on a feed roll 2, the equipment is evacuated by vacuum pump through 5, and then the specific gas is introduced into the equipment to maintain the glow discharge pressure at a predetermined level. Glow discharge is started by applying a high voltage between the electrode 6 and the roll 1. The sheet is fed from feed roll 2 and is wound by winding roll 3 through roll 1, where the sheet surface is exposed to glow discharge forming a crosslinked thin layer on the surface.

The glow discharge pressure ranges from about $10^{-2}$ to 10 torr. A glow discharge gas mixture, consisting of carbon monoxide and at least one different gas selected from the group consisting of Ar, $N_2$, $CO_2$, water, etc. is preferable. A gas mixture of CO and $CF_4$ is characteristic because it has the ability to reduce the moisture penetration coefficient as well as the plasticizer diffusion coefficient.

The electric frequency range for this treatment is about 1 to 1,000 kHz, preferably about 1 to 400 kHz.

Either of two types of glow discharge treatment may be used. One is the outside electrode type and the other is the inside electrode type. In the former, the glow discharge is maintained by a magnetic or electric field induced by electrodes such as a coil or a pair of plates attached to the outside of the equipment, usually using a high frequency of about 13.56 MHz, for example. In the latter type, the electrodes are placed inside the equipment and relatively lower frequencies can be applied to maintain the discharge.

We investigated the above mentioned two types of glow discharge for polyvinyl chloride sheet treatment. It is very surprising that the inside electrode system is much more effective in treating the polyvinyl chloride sheet than the outside electrode system. The surface treated by the inside electrode is clearly highly crosslinked and makes a good barrier in a much shorter period of treatment. These improved properties can be easily observed by both the tetrahydrofuran solution test and by gas permeation measurement. These findings clearly indicate that the inside electrode system is highly preferable.

Fluorination of the crosslinked layer can be accomplished during or after crosslinking treatment. Addition of fluorine gas or some kind of "Freon" gas to the glow discharge gas is one of the easiest ways to fluorinate the crosslinked surface. Generally, after glow discharge treatment, the formation of groups, such as —OH, =CO, and —COOH, making the surface hydrophobic, can be observed by ESCA and infrared absorption spectroscopy (ATR method). Polyvinyl chloride sheet surfaces, as well as other polymers, become wettable by glow discharge treatment. However, a glow discharge of fluorine gas, "Freon" gas or the other fluorine containing gas mixtures make the surface hydrophobic and crosslinked. Moreover, while the polyvinyl chloride sheet normally yellows as a result of glow discharge treatment, the sheet does not yellow when fluorine gas is added to the glow discharge gas.

"Freon" gas means fluorine substituted hydrocarbon and/or fluorine and other halogen substituted hydrocarbons. Glow discharge of fluorine in conjunction with other halogen substituted hydrocarbon gases, such as $CFClH_2$, is unstable and often emits uncontrollable heat. Moreover, especially when chlorine atoms are present, malodorous decomposed products form during glow discharge. On the other hand, glow discharge in the presence of fluorine substituted hydrocarbons, such as $CF_4$, $CHF_4$, and $CH_3CHF_2$, is very stable and shows excellent treatment efficiency. Gases containing unsaturated bonds, such as $C_2F_4$ and $C_2H_2F_2$, are, however, not preferred because they polymerize under the glow discharge environment. Fluorine gas has some disadvantages, such as difficulty in handling, because of its high reactivity and relatively poorer treatment efficiency, compared with "Freon" gases.

Reasonable dilution of fluorine gas and "Freon" gases with other inert gases such as CO, Ar, $N_2$, $H_2$, $O_2$, He and Ne does not affect the treatment negatively. For example, the treatment with an equimolar $CO/CF_4$ mixture gas gives almost identical effects as compared to treatment with $CF_4$ gas alone, with respect to surface tension change and reduction of plasticizer diffusion, but shows superior effects with respect to preservation of blood platelets.

Consequently, to fluorinate the surface, a "Freon" gas containing no chlorine, such as $CF_4$ and mixtures of said gas with other inert gases, are most preferable. Other inert gases may be selected to achieve optimum surface properties. The surface of polyvinyl chloride treated by an above mentioned glow discharge is analyzed by ESCA. In case of "Freon" containing gas, "peaks" representing

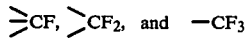

groups are observed, while in the case of fluorine gas, no —$CF_3$ peak is observed, and this is the most effective group for producing desirable hydrophobic properties. This may be one of the reasons why the treatment efficiency of fluorine gas is not satisfactory.

The thin fluorinated crosslinked layer on the surface of polyvinyl chloride acts as a good barrier with respect to not only DOP diffusion to the surface, but also to the diffusion of contents completely through the bag walls because of little chemical affinity between surface and contents. Therefore, this kind of treatment is suitable for medical apparatus such as blood bags and infusion bags.

A polyvinyl chloride sheet is exclusively used for blood bags because of its superior mechanical properties. However, as is well known, when blood is contacted with a foreign surface, undesirable effects, such as adhesion and agglomeration of platelet and gelation and coagulation of plasma, take place. So, using polyvinyl chloride blood bags of the present art, platelets coagulate on the surface reducing the number of active platelets down to 60 to 70% of the initial level after ten hours' storage. The development of new blood bags which can better preserve blood for longer periods is strongly desired in this field.

Usually, anticoagulation agents are added to bagged blood to present coagulation. These agents are classified into four types. One called ACD liquid is composed of sodium citrate as a main constituent, citric acid and dextrose. Another is CPD liquid, which comprises sodium phosphate in addition to ACD liquid. The others are heparin and EDTA liquid which is the potassium salt of ethylene-diamine-tetraacetate.

We have discovered a very characteristic phenomenon during the observation of adhesion and coagulation behavior of blood platelets to a glow discharge treated polyvinyl chloride sheet. Using scanning electron microscopy, we have discovered that the sheet showed an extremely favorable effect on the platelet's stable preservation only when ACD or CPD liquids, which contain sodium citrate as a main constituent, are used as blood preservation agents. When heparin is used as a blood preservation agent, extensive adhesion and coagulation of platelets and exsertion of pseudopodium are observed on the treated polyvinyl chloride sheet, which is comparable to the case of untreated polyvinyl chloride sheet.

Using ACD liquid, the platelet's adhesion and coagulation to the treated sheet is negligible and exsertion of pseudopodium is not observed. Of course, if the polyvinyl chloride sheet is not glow discharge treated, even through ACD liquid is used, the sheet surface is almost covered with adhering and coagulating platelets.

The reason why the combination of glow discharge treated polyvinyl chloride sheet and sodium citrate containing blood preservation agents shows this very unique and noteworthy effect on blood compatibility is not yet elucidated, but the surface may be modified to have a compatibility with sodium citrate by glow discharge treatment.

The properties of treated polyvinyl chloride sheet surface naturally depend on the glow discharge gases. Consequently, the preservation of platelets also depends on glow discharge gases. The numerous runs of experiments using different gases lead to the conclusion that a polyvinyl chloride sheet treated by the glow discharge gases, which comprise carbon monoxide and at least another gas selected from Ar, $N_2$, $CO_2$ and $H_2O$, shows an excellent effect on platelet preservation. The mixture gas of CO and $H_2O$ is especially preferable for this purpose.

On the other hand, glow discharge treatment using CO gas, while giving a better effect than the untreated sheet, was grossly inferior to the above mentioned treatment.

Though the mixture ratio of CO and other gases selected from Ar, $N_2$, $CO_2$, and $H_2O$ is decided by the parameters such as discharge stability and surface properties to be modified, a ratio greater than about 10 mol % CO is generally preferable for forming a desired thin crosslinked layer as a diffusion barrier for the plasticizer.

The blood bags of this invention must be glow discharge treated at least on the inside surfaces of the bags, but both sides should preferably be treated. Usually, the label indicating the name of the anticoagulation agent and the blood constituent and other information is attached to the outside surface of the bag. Sometimes one or more constituents of the glue for the label are believed to diffuse through the sheet and contaminate the blood. A blood bag when glow discharge treated on both surfaces has the advantage in that it removes these possibilities. For the glow discharge treatment of the outside surface of the bag, the gases are not limited as specified for the inside surface treatment, and CO, Ar or mixtures with other gases can be used.

It is usually required that carbon dioxide in the blood can be diffused out of the blood bag. Glow discharge treated blood bags in this invention have almost identical $CO_2$ permeation coefficients as the untreated bags.

The process of manufacturing blood bags in accordance with this invention can be performed in several ways. For example, the glow discharge treated sheet may be welded into bags, followed by sterilization and loading of the anticoagulation agent into the bags. Sterilization may be carried out using ethylene oxide, radiation or an autoclave because the crosslinked layer formed by glow discharge increases the heat resistance of the sheet.

As described above in detail, the blood bag in accordance with this invention is glow discharge treated or at least its inside surface in the presence of a mixture of gases comprising CO and at least one other gas selected from Ar, $N_2$, and CO. Other gases which simply dilute can be added to this gas mixture. This blood bag with an anticoagulation agent has an important advantage over both the untreated bag and the bag treated with gases other than those specified above; platelet life is extended and the number of floating platelets is reduced slowly. The original mechanical properties of the plastic sheet are not altered after treatment because of the ultra thin nature of the crosslinked layer. Further, the migration of plasticizer into the blood is dramatically minimized.

The blood bag of this invention is most suitable for use in platelet preservation. It is sometimes called a triple bag. However, because platelets are contained in whole blood and in other blood constituents, this invention is also very useful for making so-called single and double bags. If the insides of the tubes attached to this bag are glow discharge treated according to this invention the total system of the blood bag becomes preferable with respect to platelet preservation.

The polyvinyl chloride sheet in accordance with this invention provides the following superior effects and properties:

(1) The sheet does not lose its transparency after long-term thermal aging, which is a very important advantage in the use of blood bags and infusion bags. The sheets which are glow discharge treated according to the prior art gradually those their transparency because of the difference in irreversible dimension stability between the crosslinked layer and the uncrosslinked layer.

(2) The emulsion which comes into contact with the sheet surface is very stable with respect to particle size. If the emulsified lipid in a high calorie infusion procedure undergoes an increase in particle size, it may tend to block a blood vessel after administration and thus create a dangerous condition. Therefore, the sheet of this invention is especially suitable for use with high calorie infusion bags.

(3) The sheets are suitable for use in medical bags, because of dramatic suppression of diffusion of the plasticizer into its contents and of water out of the bag.

(4) The sheet has the very special property of prolonging the active lives of blood platelets contacting it.

While the sheets of this invention are especially useful for bags in the medical field, they also have a very wide range of other applications because of their unique properties. These applications include packaging foods and medicines, interior and exterior decorations, agricultural use such as greenhouse sheets, and generally wherever transparency and plasticizer diffusion are important properties.

IN THE DRAWINGS

The following examples are illustrative of the invention. They are described in specific terms which are not intended to limit the scope of this invention, which is defined in the appended claims.

EXAMPLE 1

Figure 1:
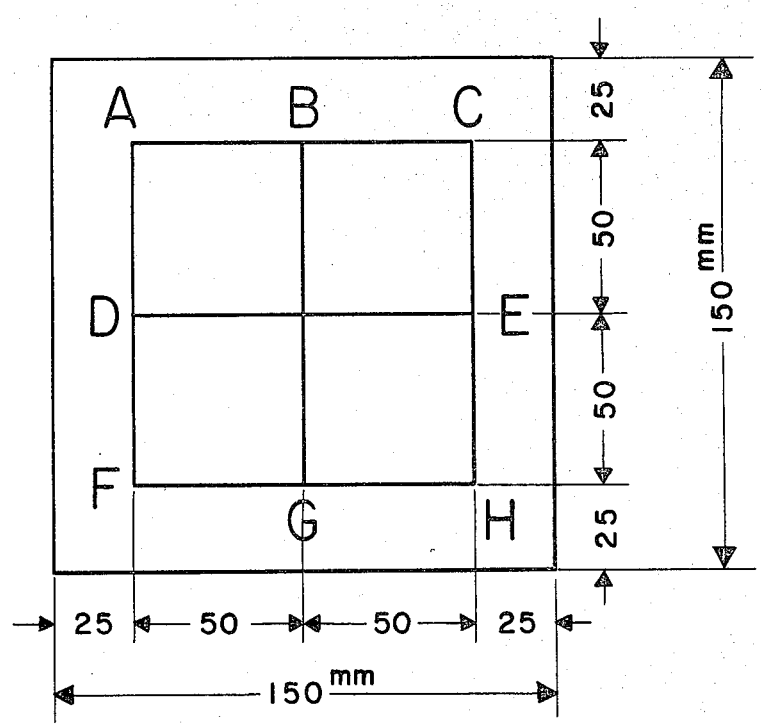
FIG. 1 shows measurement of heat shrinkage of a sheet, as heretofore described.
Figure 2:
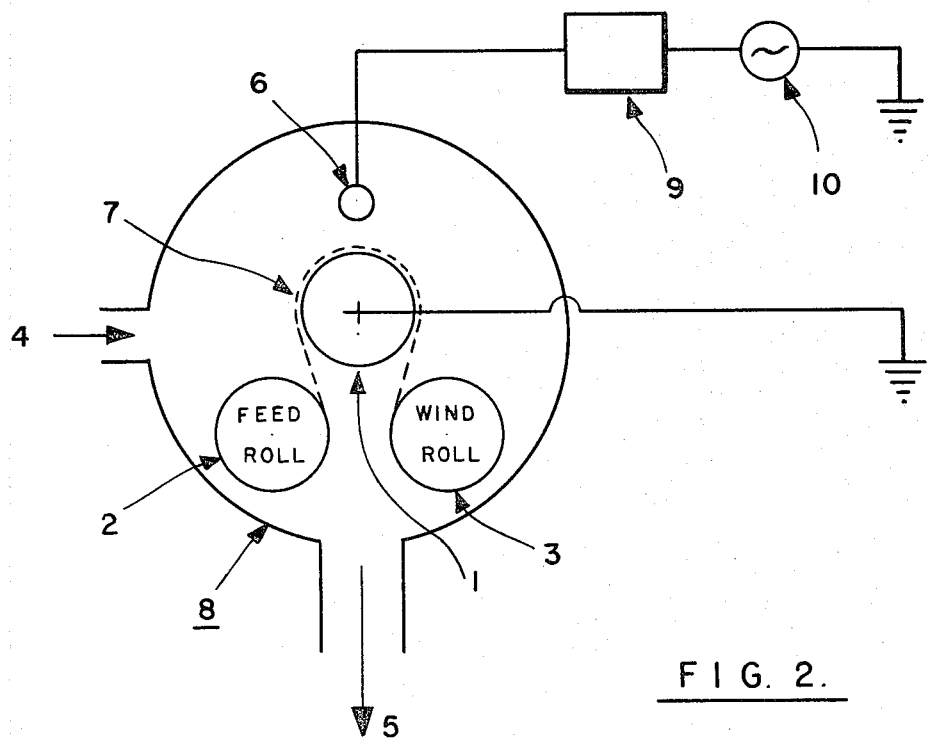
FIG. 2 illustrates diagrammatically the operation of a glow discharge machine for use in this invention.

The glow discharge machine shown in FIG. 2 was employed to treat commercially available plasticized 320 micron polyvinyl chloride sheets which contained 41 phr of DOP by weight. After the sheets were placed into the machine, the machine was degassed. Then carbon monoxide gas was introduced into the machine and the pressure of the machine was maintained at 1 torr. The sheets were subjected to gas discharge, generated by a 110-kilocycle per second high voltage oscillator at 900 W of discharge power, at various sheet speeds.

The quantity of DOP migration from sections cut from these sheets to n-hexane was measured by the method heretofore described.

Sections cut from the sheets were extracted with an excess of tetrahydrofuran at the boiling point for a period of two hours. The solvent-insoluble residue was recovered, washed with hot solvent and carefully dried. Then the amount of chlorine in the insoluble solvent residue was measured by elementary analytical methods.

After the sections cut from the sheets were dyed with osmic acid, the thickness of the crosslinked layer was measured using an electron microscope.

Figure 3:
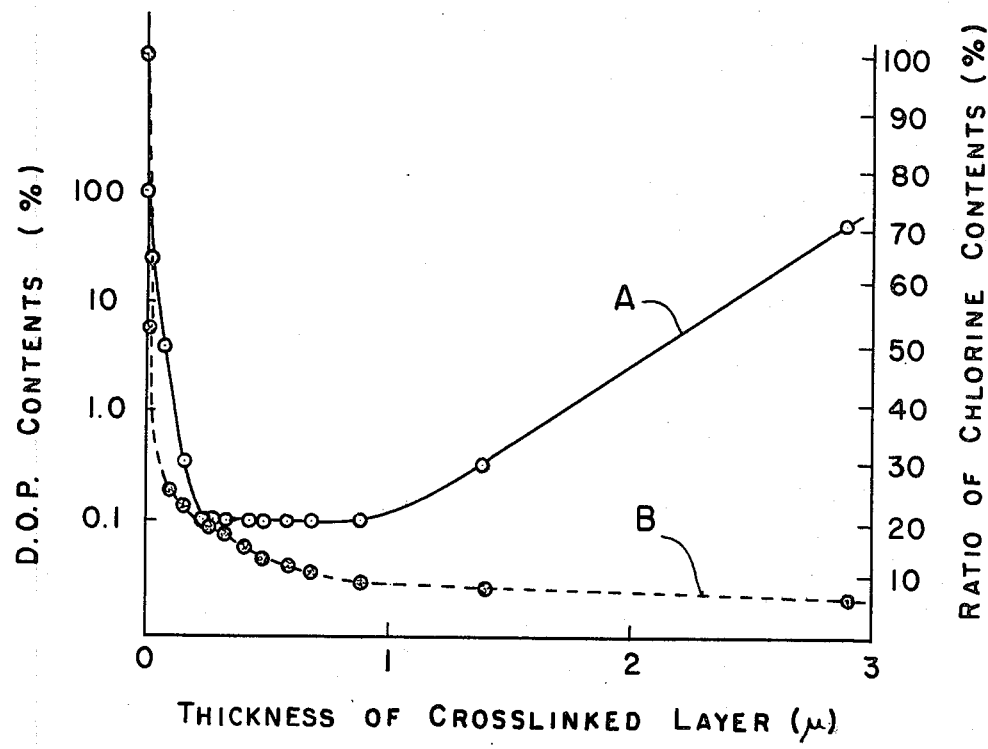
FIG. 3 is a graph which shows results of tests, as described.

These results are shown in Table 1 and FIG. 3. In FIG. 3, the curve A expresses the DOP contents of n-hexane and curve B expresses the ratio of chlorine content of the crosslinked layer to that of the uncrosslinked area.

TABLE 1

| sheet speed (m/min) | thickness of crosslinked layer ($\mu$) | ratio of chlorine contents (%) *1 | DOP contents of n-hexane (%) | Appearance of crosslinked layer |
|---|---|---|---|---|
| 0.1 | 2.9 | 6.9 | 60 | yellow needle crystals |
| 0.2 | 1.4 | 9.0 | 0.4 | yellow thin film |
| 0.5 | 0.91 | 9.7 | 0.1 | pale yellow thin film |
| 0.6 | 0.72 | 11.1 | 0.1 | pale yellow thin film |
| 0.8 | 0.58 | 12.5 | 0.1 | pale yellow |

TABLE 1-continued

| sheet speed (m/min) | thickness of crosslinked layer (μ) | ratio of chlorine contents (%) *1 | DOP contents of n-hexane (%) | Appearance of crosslinked layer |
|---|---|---|---|---|
| 1.0 | 0.51 | 13.9 | 0.1 | thin film pale yellow |
| 1.5 | 0.45 | 16.7 | 0.1 | thin film pale yellow |
| 2.0 | 0.35 | 18.1 | 0.1 | thin film pale yellow |
| 2.5 | 0.29 | 19.4 | 0.1 | thin film pale yellow |
| 3.0 | 0.27 | 20.8 | 0.1 | thin film pale yellow |
| 4.0 | 0.18 | 22.9 | 0.4 | thin film pale yellow |
| 5.0 | 0.09 | 25.0 | 5.0 | thin film pale yellow |
| 6.0 | 0.04 | 53.6 | 30.0 | thin film white thin film, slightly swollen |
| 7.5 | — | — | 57.0 | white very thin film |
| untreated | 0 | 100 | 100 | no crosslinked layer |

*1 The ratio of chlorine content of the crosslinked layer to that of uncrosslinked layer.

The appearance of the crosslinked layers shown in Table 1 indicates the presence of solvent insoluble residue. These were visually observed.

In order to reduce the migration of DOP to less than 1/10 compared with that from untreated sheet, Table 1 and FIG. 3 indicate that the ratio of chlorine contents must be under about 45% and the thickness of the crosslinked layer must be from about 0.05 micron to about 2 microns. To reduce the migration of DOP to less than 1/100, the ratio of chlorine contents must be under about 30% and the thickness of the crosslinked layer must be from about 0.1 micron to about 1 micron.

Next, untreated sheets of the same polymer as above were heatset to 150° C. for various times. Then the sheets were subjected to gas discharge under the same conditions as described above, except for sheet speed. The sheet speed was 3 m/min.

The sheets were heatset again under proper conditions to measure the heat shrinkage ratio described earlier herein. The heat shrinkage ratios of the sheets and the amount of DOP extracted with n-hexane from sections cut from the sheets were measured, and the transparencies of the sheets and the inspections for existence of waves on the surfaces of the sheets were made. These results are shown in Table 2.

Table 2 indicates that a sheet whose heat shrinkage ratio is less than about 1% maintains its transparency, even when it is heated.

EXAMPLE 2

After a plasticized 510 micron polyvinyl chloride sheet was heatset at 150° C. for two minutes, it was subjected to gas discharge under the same conditions as in Example 1, except for the sheet speed which was 2 m/min. The sheet was then heatset again under the previously described conditions to measure its heat shrinkage ratio by the method described herein. The amount of DOP extracted with n-hexane from the sheet was measured by means of gas chromatography. The transparency of the sheets was observed by the eye and the presence or absence of waves on the surface of the sheet was checked with a microscope. These results are shown in Table 3.

TABLE 2

| Heatset time (sec) | Subjected to gas discharge | Heat shrinkage ratio (%) | Transparency | Presence of waves | Amount of DOP permeated through the unit area of the sheet into n-hexane (μg/cm²) |
|---|---|---|---|---|---|
| 0 | no | 7 | transparent | absent | 1,287 |
| 0 | subjected | 6 | opaque | present | 7.1 |
| 10 | " | 4 | " | " | 8.0 |
| 30 | " | 2 | " | " | 8.0 |
| 40 | " | 1 | slightly opaque | slight | 7.0 |
| 60 | " | 0.5 | transparent | absent | 7.0 |
| 90 | " | 0 | " | " | 7.8 |

TABLE 3

| | Heatset | Subjected to gas discharge | Heat shrinkage ratio (%) | Transparency | Presence of waves | Amount of DOP permeated through the unit area of the sheet (μg/cm²) |
|---|---|---|---|---|---|---|
| Control film | no | no | 5 | transparent | absent | 1,675 |
| Control film | no | subjected | 4 | opaque | present | 0.2 |
| Film of this invention | heatset | subjected | 0 | transparent | absent | 0.2 |

EXAMPLE 3

Commercially available plasticized 320 micron polyvinyl chloride sheets, containing 41 phr of DOP by weight, were treated as described in Example 1, except that the conditions of discharge power were varied using various high voltage power supplies. Each of these power supplies delivers an alternating current of 60, 500, 1 kilo, 5 kilos, 9 kilos, 20 kilos, 110 kilos, 400 kilos and 13.56 megacycle/sec. The discharge power was 700 W, and the sheet speed was 2 m/min.

To generate gas discharge, two types of electrodes were used. One was a copper pipe having an outer diameter of 10 mm, cooled by water circulated in the pipe. The other was a copper pipe covered with glass, cooled with water circulated in the copper pipe. The outer diameter of the electrode was 10 mm.

The amount of DOP extracted with n-hexane from sections cut from the treated sheets was measured by means of gas chromatography. These results are presented in FIG. 4. Curve A indicates the results using the copper pipe as the electrode, and curve B indicates the results using the copper pipe covered with glass.

Next, a section cut from the sheets was extracted with an excess of tetrahydrofuran at the boiling point for a period of two hours. Every treated sheet comprised the solvent insoluble residue; but the solvent insoluble residue of the sheets subjected to gas discharge generated by the high voltage power supply with frequencies under 500 cycle per second and 13.5 megacycle per second, where milk-white thin films and were slightly swollen with tetrahydrofuran. The solvent insoluble residue of the sheets subjected to gas discharge generated by the high voltage power supply, of from 1 kilocycle to 400 kilocycles, were pale yellow thin films and were not swollen with tetrahydrofuran.

The phenomena described above and the results shown in FIG. 4 shows that the crosslinked layers of the sheets treated with high voltage power supply with a frequency under 400 cycles per second and 13.56 megacycles per second were not so highly crosslinked that DOP can migrate through the crosslinked layer from the inside of the sheet to n-hexane.

Figure 4:
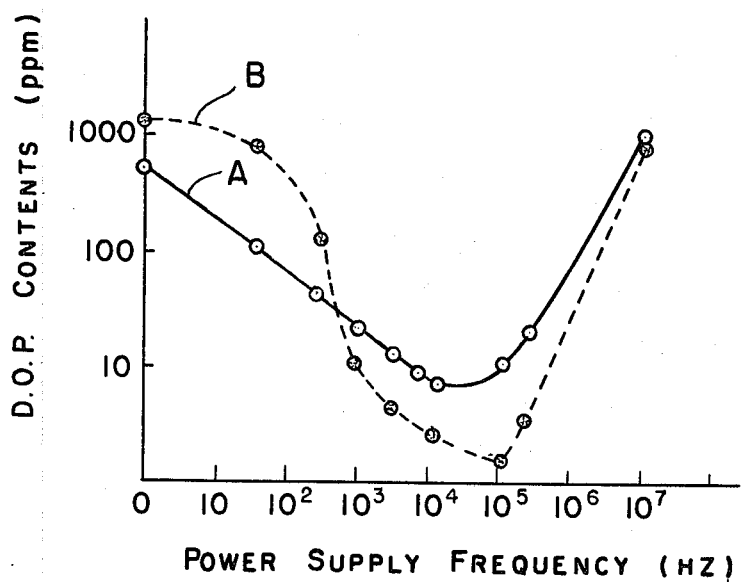
FIG. 4 is another graph.

The results, shown in FIG. 4, indicate that the optimum frequency of the power supply is from about 1 kilocycle per second to 1 megacycle per second, with the optimum frequency being from about 1 kilocycle per second to about 400 kilocycles per second. The results shown in FIG. 4 also indicate that the electrode covered with glass is the preferable electrode for generating gas discharge.

EXAMPLE 4

A medical grade 400 micron plasticized polyvinyl chloride sheet, containing 35% of DOP by weight was treated, as described in Example 1, under the conditions of pressure of 0.6 torr, discharge power of 900 W, and sheet speed of 1 m/min, using a mixed gas consisting of $CF_4$ (40% by mol) and CO (60% by mol).

As a control sample, a sheet of the same polymer was treated as described above, but using CO gas.

Sections cut from these sheets were extracted with an excess of tetrahydrofuran at the boiling point for a period of two hours. The solvent insoluble residue was recovered, washed with hot solvent and dried. The solvent insoluble residue of the sheet subjected to CO gas discharge was a thin yellow film, but that of the sheet subjected to the mixed gas discharge was a thin white film.

Small infusion bags were made from these sheets and from the sheet which was not subjected to gas discharge. These bags were filled with n-hexane and stored in a constant temperature box at 40° C. for two hours, and then the amount of DOP in n-hexane in each bag was measured by means of gas chromatography. The results are shown in Table 4.

Other bags were filled with a constant weight of water and then weighed. These bags were stored in a room at a constant temperature of 20° C. and at a constant relative humidity of 65% for two weeks. Then these bags were weighed. The weight loss of water in the bags was calculated from these data. These results are shown in Table 4.

TABLE 4

| sheet formed into bag | amount of DOP permeated through the unit area of the sheet ($\mu g/cm^2$) | weight loss of water in the bag (W %) |
|---|---|---|
| control sheet | 3,921 (100%) | 5.7 |
| sheet subjected to CO gas discharge | 175 (4.4%) | 4.4 |
| sheet subjected to CO—$CF_4$ mixed gas discharge | 122 (3.1%) | 0.19 |

The results shown in Table 4 indicate that the amounts of DOP and water diffused through the sheet subjected to CO—$CF_4$ mixed gas discharge are smaller than those of the control sheet.

EXAMPLE 5

A sheet of the same polymer used in Example 4, was treated as described in Example 4, except that a mixed gas, consisting of $CF_4$ (60% by mol) and CO (40% by mol), was used. As a contrast sample, a sheet of the same polymer was treated as described in Example 4, using only CO gas.

Small infusion bags were made from these sheets and from the control sheet and then sterilized with ethylene oxide gas.

These bags were filled with emulsifying lipid commercially available under the Trademark Intralipid 10% from Green Cross Co., Japan, and then stored in a room for seventy-two hours. Then the DOP content of the emulsifying lipid was measured by the procedure described below. 40 cc of n-hexane was added to 10 cc of the emulsifying lipid, the mixture was shaken, then the n-hexane was separated from the emulsifying lipid and the same procedure was repeated twice. Next, all of the n-hexane was dehydrated and distilled off at reduced pressure. 10 cc of n-hexane and di-n-cotyl phthalate, as internal standard material, were added to the residue and the DOP content of the mixture was measured by means of gas chromatography. The results are shown in Table 5.

Particle diameters of the emulsifying lipid in the bags were measured by the procedure described below. 150 cc of water were added to 0.1 cc of the emulsifying lipid in the bag and then 150 cc of water containing 20% sodium chloride by weight were added. The number of particles of emulsifying lipid with a particle diameter greater than 1.5 microns was measured with a Coulter counter.

The particles of the emulsifying lipid increased in size with time upon the addition of the water containing sodium chloride. Thus, the measurements were finished within three minutes after adding the water containing sodium chloride. The results are shown in Table 5.

TABLE 5

| Bag | DOP content of n-hexane (ppm) | number of particles of emulsifying lipid (number/0.5 cc) beyond 1.5$\mu$ | beyond 4$\mu$ |
|---|---|---|---|
| Bag made of control sheet | 6 | 24.392 | 13.0 |
| Bag made of the sheet subjected to CO gas discharge | non-detectable | 14.857 | 9.7 |
| Bag made of the sheet subjected to CO—$CF_4$ mixed gas | non-detectable | 12.476 | 4.7 |

TABLE 5-continued

| Bag | DOP content of n-hexane (ppm) | number of particles of emulsifying lipid (number/0.5 cc) | |
|---|---|---|---|
| | | beyond 1.5μ | beyond 4μ |
| discharge | | | |

The results shown in Table 5 indicate that the amount of DOP diffused to n-hexane from the bag made of the sheet subjected to CO—$CF_4$ mixed gas discharge is small and the particles of emulsifying lipid hardly increase in size in the bag made of the sheet subjected to CO—$CF_4$ mixed gas discharge.

EXAMPLE 6

Sheets cut from the blood bag made of plasticized polyvinyl chloride, commercially available under the Trademark Telflex BB-T060CJ from Termo Co., Japan, were put on drum 1 in the glow-discharge machine shown in FIG. 2 and then were subjected to Ar gas discharge under a pressure of 0.6 torr, a discharge power of 1,200 W, and a sheet speed of 1 m/min.

A section cut from the sheet was extracted with an excess of tetrahydrofuran at the boiling point for two hours. The insoluble residue appeared in the n-hexane. A measurement of the work of adhesion to water, taken on the treated sheet and a control sheet, was carried out. The work of adhesion of the treated sheet was 118 dyne/cm and that of the control sheet was 91 dyne/cm.

9 $cm^2$ of section cut from the sheet subjected to the gas discharge and a control sheet were immersed in blood consisting of 7 ml of blood drawn from a carotid artery of a rabbit and 1.5 ml of ACD solution consisting of 2.20 g of sodium citrate, 0.80 g of citric acid, 2.20 g of dextrose and distilled water to form 100 ml of solution, and shaken at 100 rpm in a constant temperature box of 37° C. for thirty minutes. Then, the blood was rotated at 1,200 rpm for thirty minutes and separated centrifugally. The number of platelets in the supernatant liquid was measured with a Coulter counter. The results are shown in Table 6. The number of platelets was expressed in proportion to the number of platelets of blood in which the control sheet was immersed. The control sheet ratio was expressed as 100%.

TABLE 6

| Sheet | ratio of the number of platelet (%) |
|---|---|
| Control sheet | 100 |
| Sheet subjected to gas discharge | 137 |

Next, the remainder of the blood containing the supernatant liquid was rotated at 3,600 rpm and separated contrifugally. Then, 5 ml of physiological salt solution was added to 1 ml of the supernatant liquid of the blood. The absorbency of the solution at 545 mili-microns was measured. The absorbency of the blood in which the sheets were immersed was the same for any kind of sheet. Therefore, no hemolysis of the blood, in which the sheet subjected to gas discharge was immersed, was recognized.

The sheets immersed in the blood were washed with 10 ml of physiological salt solution five times, fixed with a solution consisting of 9% formaldehyde and 91% physiological salt solution, and the observed with a scanning electron microscope.

The control sheet was convered with many platelets, but the sheet subjected to gas discharge was covered with only a few.

The results described above show that the bag, made from the plasticized polyvinyl sheet subjected to gas discharge and containing an anticoagulation agent comprising sodium citrate, is more suitable for blood bag.

EXAMPLE 7

Two 9 $cm^2$ sections, one cut from a sheet treated as described in Example 6 and another control sheet, were immersed in 7 ml of blood which consisted of blood drawn from a carotid artery of a rabbit and 6 units per ml of heparin, shaken at 100 rpm in a constant temperature box of 37° C. for thirty minutes.

The number of platelets in the blood was measured by the method described in Example 6. The results are shown in Table 7.

TABLE 7

| Sheet | ratio of the number of platelets (%) |
|---|---|
| Control sheet | 100 |
| Sheet subjected to gas discharge | 106 |

Hemolysis was investigated by the method described in Example 6. No hemolysis of the blood, in which the sheet subjected to gas discharge was immersed, was recognized.

The sheets were fixed using the same method described in Example 6 and were observed with a scanning electron microscope. Both the control sheet and the sheet subjected to gas discharge were covered with many platelets with some of the platelets adhering to the sheets in aggregated and exserted pseudopodium forms.

The results described above imply that heparin, as an anticoagulant, is less suitable for a blood bag made from the polyvinyl chloride sheet subjected to gas discharge.

EXAMPLE 8

A medical grade plasticized polyvinyl chloride sheet, containing 35% of DOP by weight, was treated as described in Example 1, but at a sheet speed of 1.2 m/min.

The blood, which consisted of 91% blood drawn from a carotid artery of a rabbit and 9% anticoagulation agent by weight consisting of 3.8% of sodium citrate and 96.2% of physiological salt solution by weight, was shaken at 1,200 rpm and separated centrifugally to make platelet enriched plasma supernatant liquid.

Two 4 $cm^2$ sections, one cut from the sheet subjected to gas discharge and the other a control sheet, were immersed in the platelet enriched plasma, stored in an incubator filled with carbonic acid gas at a constant temperature of 37° C. for two hours, then washed with a solution which consisted of 10% phosphate buffer having a pH of 7.4 and 90% physiological salt solution, fixed with a solution consisting of 9% formaldehyde and 91% physiological salt solution, and observed with a scanning electron microscope.

The control sheet was completely covered with many platelets. Most were aggregated, but platelets covered only a small part of the sheet subjected to gas discharge and only a few were aggregated.

The results show that sodium citrate, as an anticoagulant, is suitable for a bag made from the polyvinyl chloride sheet subjected to gas discharge. The results of this example and Example 8 imply that a bag, made from the polyvinyl chloride sheet subjected to gas discharge and containing an anticoagulant comprising sodium citrate, is suitable for storing whole blood and components of blood.

EXAMPLE 9

A sheet of the same polymer used in Example 8 was formed without heat-setting. Its heat shrinkage ratio was 3%.

The same sheet that was used in Example 8, having a 0.3% heat shrinkage ratio, and the sheet described above, were treated as described in Example 8.

Small blood bags were made from these sheets, then filled with 10 ml of ACD solution, sterilized in an autoclave at 121° C. for twenty-five minutes and then allowed to cool.

The bag made from the sheet with a 0.3% heat shrinkage ratio was sufficiently transparent to easily check the content's turbidity and for the presence of suspended solids in the ACD solution, but the bag made from the sheet with a 3% heat shrinkage ratio was opaque, so it was very difficult to check the content's turbidity and for the presence of suspended solids in the ACD solution.

We claim:

1. A polyvinyl chloride sheet comprising an uncrosslinked portion having on a surface thereof a crosslinked layer having a thickness of about 0.05 to about 2 microns, said crosslinked layer having a degree of chlorination of about 45% or less as compared to the degree of chlorination of the uncrosslinked portion of the sheet, and said sheet having a heat shrinkage of about 1% or less.

2. The polyvinyl chloride sheet of claim 1, wherein said crosslinked layer is partially fluorinated.

3. The polyvinyl chloride sheet of claim 2, wherein the number of fluorine atoms is 10% or more as compared to the number of carbon atoms on the crosslinked surface.

4. An infusion bag made of a polyvinyl chloride sheet of claim 1.

5. The infusion bag of claim 4, wherein the crosslinked layer is partially fluorinated.

6. The infusion bag of claim 5, wherein the number of fluorine atoms is about 10% or more as related to the number of carbon atoms on the crosslinked surface.

7. A blood bag comprising a polyvinyl chloride bag made from the sheet of claim 1, and with anticoagulation agents in said bag containing sodium citrate as a main constituent.

8. The blood bag of claim 7, wherein the crosslinked layer is partially fluorinated.

9. The blood bag of claim 8, wherein the number of fluorine atoms is about 10% or more, as related to the number of carbon atoms on the crosslinked surface.

* * * * *